(12) United States Patent
Timsit et al.

(10) Patent No.: US 8,318,707 B2
(45) Date of Patent: Nov. 27, 2012

(54) ADMINISTRATION OF (S)-ROSCOVITINE FOR PROTECTION AGAINST AND/OR TREATMENT OF NEUROLOGICAL DISEASES

(75) Inventors: Serge Timsit, Brest (FR); Bénédicte Menn, Marseilles (FR); Laurent Meijer, Roscoff (FR)

(73) Assignee: Neurokin, Marseilles (FR)

( * ) Notice: Subject to any disclaimer, the term of this patent is extended or adjusted under 35 U.S.C. 154(b) by 708 days.

(21) Appl. No.: 12/225,834

(22) PCT Filed: Mar. 30, 2007

(86) PCT No.: PCT/FR2007/000558
§ 371 (c)(1),
(2), (4) Date: May 7, 2009

(87) PCT Pub. No.: WO2007/118984
PCT Pub. Date: Oct. 25, 2007

(65) Prior Publication Data
US 2010/0008927 A1 Jan. 14, 2010

(30) Foreign Application Priority Data
Mar. 30, 2006 (FR) ..................... 06 02773

(51) Int. Cl.
*A01N 43/00* (2006.01)
*A61K 31/55* (2006.01)
*A61K 31/52* (2006.01)
(52) U.S. Cl. ................. 514/161; 514/215; 514/263.4
(58) Field of Classification Search .................. None
See application file for complete search history.

(56) References Cited

U.S. PATENT DOCUMENTS

| | | | |
|---|---|---|---|
| 6,316,456 | B1 | 11/2001 | Meijer et al. |
| 2002/0042412 | A1 | 4/2002 | Zaharevitz et al. |
| 2002/0049218 | A1 | 4/2002 | Meijer et al. |
| 2003/0060397 | A1 | 3/2003 | Timsit et al. |
| 2003/0069259 | A1 | 4/2003 | Borcherding et al. |
| 2003/0105075 | A1 | 6/2003 | Meijer |
| 2003/0114672 | A1 | 6/2003 | Gray et al. |
| 2003/0176699 | A1 | 9/2003 | Gray et al. |
| 2003/0181439 | A1 | 9/2003 | Meijer et al. |
| 2003/0186999 | A1 | 10/2003 | Meijer et al. |
| 2004/0235868 | A1 | 11/2004 | Meijer et al. |
| 2004/0254094 | A1 | 12/2004 | Albrecht et al. |
| 2005/0080097 | A1 | 4/2005 | Moravcova et al. |
| 2006/0148829 | A1 | 7/2006 | Meijer et al. |
| 2007/0110751 | A1* | 5/2007 | MacLellan et al. ........ 424/146.1 |
| 2007/0275986 | A1 | 11/2007 | Becq et al. |
| 2008/0161312 | A1 | 7/2008 | Meijer et al. |
| 2009/0030019 | A1 | 1/2009 | Meijer et al. |

FOREIGN PATENT DOCUMENTS

| | | |
|---|---|---|
| EP | 0 911 634 A | 4/1999 |
| EP | 1 348 707 A | 10/2003 |
| WO | 97/20842 A | 6/1997 |
| WO | 01/70231 A | 9/2001 |
| WO | 2004/026246 A | 4/2004 |
| WO | 2006/021803 A | 3/2006 |

OTHER PUBLICATIONS

Wang et al. Mechanisms of hemorrhagic transformation after tissue plasminogen activator reperfusion therapy for ischemic stroke. Stroke. Nov. 2004;35(11 Suppl 1):2726-30. Epub Sep. 30, 2004.*
DeLaGarza et al. Pharmacologic treatment of Alzheimer's disease: an update. Am Fam Physician. Oct. 1, 2003;68(7):1365-72.*
Albers et al. Antithrombotic and thrombolytic therapy for ischemic stroke: the Seventh ACCP Conference on Antithrombotic and Thrombolytic Therapy. Chest. Sep. 2004;126(3 Suppl):483S-512S.*
Vickers. A vaccine against Alzheimer's disease: developments to date. Drugs Aging 2002; 19(7):487-94.*
"Racemic Substance." Hawleys Condensed Chemical Dictionary, 13th ed (1997), p. 952, Richard J. Lewis (Editor).*
Moss. Basic Terminology of Stereochemistry. Pure Appl Chem vol. 68. 2193-2122, (1996).*
Mapelli, Marina et al: "Mechanism of CDK5/p25 binding by CDK inhibitors," Journal of Medicinal Chemistry, vol. 48, No. 3, Feb. 10, 2005, pp. 671-679, XP002402136, ISSN: 0022-2623.
Beart, P. M. et al.: "Roles for cyclin-dependent and mitogen-activated protein kinases in kainate receptor-mediated apoptosis," Society for Neuroscience Asbtracts, vol. 26, No. 1-2, 2000, pp. Abstract No.-702. 3, XP008069586 & 30$^{th}$ Annual Meeting of the Society of Neuroscience; New Orleans, LA, USA; November 4-9, 2000, ISSN: 0190-5295.
Bach, Stephane et al.; "Roscovitine targets, protein kinases and pyridoxal kinase," Journal of Biological Chemistry, vol. 280, No. 35. Sep. 2005, pp. 31208-31219, XP002402137, ISSN: 0021-9258.
Olney, John W. et al.; "Cell Death and Diseases of the Nervous System;" Humana Press Inc., 1999; pp. 197-219.
Choi, Dennis W.; "Calcium-Mediated Neurotoxicity: Relationship to Specific Channel Types and roles in Ischemic Damage;" Trends Neurosci., vol. 11, No. 10, 1988; pp. 465-469.
Coyle Joseph T. et al.; "Oxidative Stress, Glutamate, and Neurodegenerative Disorders;" Science, vol. 262, Oct. 29, 1993; pp. 689-695.

(Continued)

*Primary Examiner* — Gregory S Emch
(74) *Attorney, Agent, or Firm* — Harness, Dickey & Pierce, P.L.C.

(57) ABSTRACT

The present invention relates to the use of 6-(benzyl-amino)-2(S)-[[1-(hydroxymethyl) propyl]amino]-9-isopropylpurine) or at least one of its pharmaceutical acceptable salts for manufacturing a medication intended for the prevention and/or treatment of neurological diseases, in particular associated with neurological lesions.

20 Claims, 5 Drawing Sheets

OTHER PUBLICATIONS

Lipton, Stuart A. et al.; "Excitatory Amino Acids as a Final Common Pathway for Neurologic Disorders;" The New England Journal of Medicine, vol. 330, No. 9, Mar. 3, 1994, file://D:\documents\Lipton-1994-NEJM.htm; pp. 613-622.

Vermeulen, Katrien et al.; "The Cell Cycle: A Review of Regulation, Deregulation and Therapeutic Targets in Cancer;" Cell Proliferation, vol. 36, No. 3, 2003; pp. 131-149.

De Azevedo, Walter F. et al.; "Inhibition of Cyclin-Dependent Kinases by Purine Analogues Crystal Structure of Human cdk2 Complexed with Roscovitine;" Eur. J. Biochem., 243, 1997; pp. 518-526.

Busser, Jonathan et all; "Ectopic Cell Cycle Proteins Predict the Sites of Neuronal Cell Death in Alzheimer's Disease Brain;" The Journal of Neuroscience, vol. 18, No. 8, Apr. 15, 1998; pp. 2801-2807.

Havlíček, Libor et al.; "Cytokinin-Derives Cyclin-Dependent Kinase Inhibitors: Synthesis and cdc 2 Inhibitory Activity of Olomoucine and Related Compounds;" J. Med. Chem., vol. 40, No. 4, 1997; pp. 408-412.

Wang, Shudong et al.; "Synthesis and Configuration of the Cyclin-Dependent Kinase Inhibitor Roscovitine and its Enantiomer;" Tetrahedron: *Asymmetry*, 12 (20), 2001; pp. 2891-2894.

Portera-Cailliau, Carlos et al.; "Non-NMDA and NMDA Receptor-Mediated Excitotoxic Neuronal Deaths in Adult Brain are Morphologically Distinct: Further Evidence for an Apoptosis-Necrosis Continuum;" The Journal of Comparative Neurology, 378, 1997; pp. 88-104.

Reisberg, M.D., Barry et al.; "Memantime in Moderate-to-Severe Alzheimer's Disease;" The New England Journal of Medicine, 348 (14), Apr. 3, 2003; pp. 1333-1341.

Medina, Igor et al.; "Kainate-Induced Inactivation of NMDA Currents Via an Elevation of Intracelleular $Ca^{2+}$ in Hippocampal Neurons;" Journal of Neurophysiology, vol. 72, No. 1, Jul. 1994; pp. 456-465.

Stoppini, L. et al.; "A Simple Method for Organotypic Cultures of Nervous Tissue;" Journal of Neuroscience Methods, 37 (2), 1991; pp. 173-182.

Muller, D. et al.; "Time Course of Synaptic Development in Hippocampal Organotypic Cultures;" Developmental Brain Research, 71 (1), Jan. 15, 1993; pp. 93-100.

Buchs, P.-A. et al.; "Structural Modifications Associated with Synaptic Development in Area CA1 of Rat Hippocampal Organotypic Cultures;" 71 (1), Jan. 15, 1993; pp. 81-91.

Tamura, A. et al.; "Focal Cerebral Ischaemia in the Rat: 1. Description of Technique and Early Neuropathological Consequences Following Middle Cerebral Artery Occlusion;" Journal of Cerebral Blood Flow and Metabolism, vol. 1, No. 1, 1981; pp. 53-60.

Guégan, Christelle et al.; "Recruitment of Several Neuroprotective Pathways After Permanent Focal Ischemia in Mice;" Experimental Neurology, vol. 154, 1998; pp. 371-380.

Guégan, Christelle et al.; "Reduction of Cortical Infarction and Impairment of Apoptosis in NGF-Transgenic Mice Subjected to Permanent Focal Ischemia;" Molecular Brain Research, vol. 55, 1998; pp. 133-140.

Blanche, P., et al: "Devic's neuromyelitis optima and HIV-1 infection," J Neurol Neurosurg Psychiatry 2000;68:795-796.

* cited by examiner

ADMINISTRATION OF (S)-ROSCOVITINE FOR PROTECTION AGAINST AND/OR TREATMENT OF NEUROLOGICAL DISEASES

CROSS-REFERENCE TO RELATED APPLICATIONS

This application is a National Stage of International Application No. PCT/FR2007/000558, filed Mar. 30, 2007, claiming priority to FR 06/02773, filed Mar. 30, 2006, both of which are incorporated by reference herein.

BACKGROUND AND SUMMARY

The present invention relates to the field of the treatment and prevention of neurological diseases, in particular associated with neurological lesions linked in particular to the phenomenon of excitotoxicity. It relates more particularly to a novel therapeutic application of (S)-roscovitine, the chemical name of which is 6(benzylamino)2(S) [[hydroxymethyl)propyl]amino]-9-isopropylpurine).

Excitotoxicity corresponds to an accumulation of excitatory amino acids that excessively activate the glutamate receptors leading to neurone death (Olney J W and Ishimaru M J, 1999; Excitotoxic cell death. Cell death and diseases of the nervous system, Humana Press Inc: 197-219). Excitatory amino acids represent a group of structural analogues of glutamate comprising numerous members including aspartate, kainate and some of its derivatives, known to represent powerful neurone exciters. Glutamate is indisputably the best characterised excitatory amino acid. The effect of excitatory amino acids is transmitted by the metabotropic and ionotropic glutamate receptors of the NMDA, AMPA and kainate type.

Excitotoxicity thus plays a major role in the development of neurological lesions associated with numerous neurological diseases, in particular acute and chronic neurological diseases. (Choi, 1988, Trends Neurosci, vol 11, pages 465-459; Coyle and Puttfarcken, 1993, Science, vol. 262, pages 689-695; Lipton and Rosenberg, 1994, New Engl J Med, vol. 330, pages 613-622). It is therefore advantageous to identify and characterise neuroprotective compounds for preventing and/or treating neurological lesions in particular relating to the phenomenon of excitotoxicity.

The use of the R isomer and the racemic mixture of roscovitine in the treatment of neurone apoptosis has been described previously in European patent EP 0 874 847. This patent reveals the anti-mitotic properties of roscovitine and in particular its inhibitory action on various cyclin-dependent kinase (cdk) proteins involved in the cell division cycle or apoptosis. On the basis of the results, and relying on the known relationships between the cell division cycle and apoptosis (Vermeulen et al, Cell Prolif. 2003 vol. 36(3), pages 131-49), the authors of this patent have suggested a possible effect of roscovitine on neurone apoptosis. Although some compounds are already used for treating neurological lesions, they may have side effects, such as a certain toxicity or insufficient efficacy. Therefore, there remains a need for compounds having improved properties for treating neurological lesions.

Surprisingly, the inventors have discovered that the S isomer of roscovitine makes it possible to wholly or partially resolve the above-mentioned deficiencies, and that it has a better neuroprotective efficacy than the R isomer. Thus the inventors have now identified and characterised a particular compound, (S)-roscovitine, for effectively preventing and/or treating neurological lesions linked in particular to the phenomenon of excitotoxity. This neuroprotective effect of (S)-roscovitine is particularly unexpected. Specifically, (S)-roscovitine inhibits various cyclin-dependent kinase (cdk) proteins involved in the cell division cycle or apoptosis more weakly than (R)-roscovitine. In particular, the inhibitory activity of (S)-roscovitine on cdk-5, cdk-1/cyclin B and cdc2/cyclin B kinase proteins is lower than that of (R)-roscovitine (De Azevedo et al., Eur. J. Biochem. 243, 518-526, 1997; Bach et al, The Journal of Biochemical Chemistry, 280, 35, 31208-31219). Incidentally, these kinase proteins, in particular cdk-5 and cdc2/cyclin B, are known for their role in neurone death (Dhavan and Tsai, 2001; Busser et al. 1998).

According to a first aspect, an object of the invention is the use of (S)-roscovitine or 6-(benzyl-amino)-2(S)-[[1-(hydroxymethyl)propyl]amino]-9-isopropylpurine) or at least one of its pharmaceutically acceptable salts for manufacturing a medication intended for the prevention and/or treatment of neurological diseases. "(S)-roscovitine" refers to the compound of the following formula:

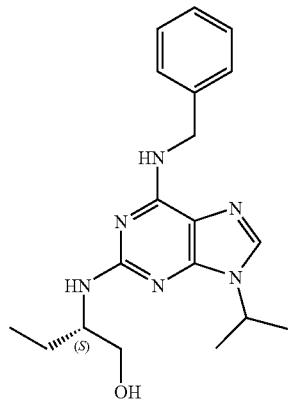

6-(benzyl-amino)-2(S)-[[1-hydroxymethyl)propyl]amino]-9-isopropylpurine), in particular in an enantiomeric excess greater than or equal to 90%, in particular greater than or equal to 95%, especially greater than or equal to 99%, or even greater than or equal to 99.5%.

The enantiomeric excess can be defined by the formula ((S)-roscovitine−(R)-roscovitine/(S)-roscovitine+(R)-roscovitine)×100.

(S)-roscovitine can be obtained according to methods well known to persons skilled in the art, for example by a three-step synthesis from 2,6-dichloropurine as described by Havlicek et al (J. Med. Chem, 1997, 40, 408) and by Wang et al (Tetrahefron: Asymmetry, 2001, 12, 2891). (S)-roscovitine is also available from Alexis Corporation under reference N° ALX-350-293-M001. "Pharmaceutically acceptable salts" refers to salts suitable for pharmaceutical use. Examples of pharmaceutically acceptable salts include benzene sulfonate, bromhydrate, chlorhydrate, citrate, ethanesulfonate, fumarate, gluconate, iodate, isethionate, maleate, methanesulfonate, methylene-bis-b-oxynaphthoate, nitrate, oxalate, pamoate, phosphate, salicylate, succinate, sulphate, tartrate, theophyllinacetate and p-toluenesulfate. The pharmaceutically acceptable salts of (S)-roscovitine can be obtained by methods well known to persons skilled in the art.

Generally "neurological disease" refers to a disease characterised by "neurological lesions". "Neurological lesions" refers to a structural alteration in the nervous system in its anatomical and physiological characteristics. The lesion may be microscopic or macroscopic. The lesion may be of traumatic origin or caused by a disease, in particular by acute or chronic neurological diseases. These neurological lesions may affect various cell types, neurones, astrocytes, oligodendrocytes, microglia and progenitors of these cells.

In some cases, the neurological lesions are linked to the phenomenon of excitotoxicity.

In particular, the prevention and/or treatment of neurological lesions is associated with the neuroprotection activity of (S)-roscovitine. "Neuroprotection" refers to the ability of a compound to prevent the death of healthy and/or ailing neural cells. Neural cells refer to the cells of the nervous system and in particular of the brain. These neural cells may in particular be chosen from neurones, astrocytes and oligodendrocytes.

Neuroprotection is particularly advantageous in the case of neurological ailments, in particular acute or chronic neurological ailments. Specifically, these ailments may be associated with neural cell degeneration leading to cell death. This may thus make it possible the use of compounds for preventing and/or delaying the death of these neural cells, or at least some of these neural cells, healthy and/or ailing. For example, after a stroke some neural cells die immediately, or almost immediately, thereby defining a so-called "necrotic core". However, there also exists a so-called "penumbra" zone, juxtaposing the necrotic core, in which the cells may be progressively affected before reaching cell death. The use of certain neuroprotective therapeutic agents may prevent the process of at least some of these cells towards neural death.

According to a particular embodiment of the use according to the invention, the neurological diseases are chronic neurological diseases. "Chronic neurological diseases" refer to neurological diseases the symptoms of which may be initially slight but which may progressively develop and worsen, for example over several years.

Among chronic neurological diseases the following can be cited:

neurodegenerative diseases (Adams and Victor; Third edition; McGraw-Hill book company; 1995) comprising:

diseases with extrapyramidal syndrome, in particular Parkinson's disease, progressive supranuclear paralysis (Steel-Richardson and Olzewski syndromes), multiple system atrophy and striatonigral degeneration;

dementias, in particular Alzheimer's disease, vascular dementias, Lewy body disease, frontotemporal dementias, cortico-basal degeneration and Huntington's chorea, and other neurodegenerative diseases, in particular amyotrophic lateral sclerosis and Creutzfeld-Jakob disease (Choi, 1988; Coyle and Puttfarcken, 1993; Lipton and Rosenberg, 1994);

demyelinating diseases, in particular multiple sclerosis, disseminated acute allergic encephalitis, Devic's disease (neuromyelitis optica) and genetic diseases with affliction of the myelin, in particular Pelizaeus-Merzbacher disease.

According to another particular embodiment, neurological diseases are acute neurological diseases, in particular ischemic cerebral vascular accident.

"Acute neurological diseases" refer to neurological diseases the symptoms and clinical signs of which may initially be very marked and may stabilise rapidly, for example after a few days. Acute neurological diseases comprise:

epilepsy;
status epilepticus;
stroke, in particular ischemic;
cerebral haemorrhages;
cerebral hypoxia during cardiac arrests;
cranial traumatisms, and neurological diseases causing focal and/or global cerebral hypoxia, occurring in particular during extracorporeal circulations, in particular during cardiac and/or vascular interventions and carotid surgery.

Cerebral haemorrhages refer to intraparenchymatous haemorrhages and meningeal haemorrhages. After meningeal haemorrhage an ischemia may occur in relation to the vasospasm. (S)-roscovitine could prevent or reduce cerebral ischemia following a meningeal haemorrhage.

In particular, certain cerebral haemorrhages may be linked to the use of a thrombolytic agent, in particular tissue plasminogen activator (t-PA). Specifically, thrombolytic agents used in the first hours of an ischemic stroke may cause cerebral haemorrhages. These cerebral haemorrhages represent a major side effect of thrombolosis during ischemic accident. (S)-roscovitine could therefore be advantageous in association with a thrombolytic agent for reducing the risk of occurrence of a cerebral haemorrhage by protecting the haematoencephalic barrier. (S)-roscovitine could act as an anti-aptopic agent in cerebral endothelial cells. Cerebral endothelial cells are one of the major components of the haematoencephalic barrier.

The medication according to the invention may further comprise at least one anti-neurodegenerative agent, in particular an agent intended for combating and/or preventing chronic and/or acute neurological disease and more particularly ischemic stroke. "Anti-neurodegenerative agent" refers to a compound for combating and/or preventing nervous system degeneration. Examples of anti-neurodegenerative agent include acetylcholinesterase inhibitors such as donepazil, selegiline, rivastigmine and galantamine, and antiglutamatergics such as memantine and riluzole. Thus, (S)-roscovitine can be used in association with an anticholinesterasic medication (donepezil, rivastigmine, galantamine) or an anti-glutamatergic medication (memantine) for Alzheimer's disease or other dementias, such as vascular dementia, Lewy body disease, fronto-temporal dementias, cortico-basal degeneration, Huntington's chorea or Parkinsonian dementia .... (S)-roscovitine could be used in association with riluzole for amyotrophic lateral sclerosis.

(S)-roscovitine and the anti-neurodegenerative agent can be administered simultaneously, separately or staged over time. (S)-roscovitine and the anti-neurodegenerative agent can be present in the medication according to the invention in a molar ratio ranging from 10/1 to 1/10.

The medication according the invention can further comprise at least one thrombolytic agent. "Thrombolytic agent" refers to a substance capable of lysing blood clots, such as tissue plasminogen activator (t-PA), streptokinase, urokinase and desmoteplase. (S)-roscovitine and the thrombolytic agent can be administered simultaneously, separately or staged over time. (S)-roscovitine and the thrombolytic agent can be present in the medication according to the invention in a molar ratio ranging from 100/1 to 1/100.

Thrombolytic agents may have side effects. They may for example cause cerebral haemorrhages. The use of (S)-roscovitine in combination with at least one thrombolytic agent, in particular t-PA, may reduce some of these side effects, and in particular the risk of cerebral haemorrhage.

The medication according to the invention may further comprise at least one platelet aggregation inhibiting agent. Examples of "platelet aggregation inhibiting agent" include acetylsalicylic acid, ticlopidine hydrochlorate, clopidogrel, dipyridamole, abciximab and flurbiprofen. (S)-roscovitine can be used in combination with a platelet aggregation inhibiting agent for ischemic stroke. (S)-roscovitine and the platelet aggregation inhibiting agent can be administered simultaneously, separately or staged over time. (S)-roscovitine and the platelet aggregation inhibiting agent can be present in the medication according to the invention in a molar ratio ranging from 10/1 to 1/10.

The medications according to the invention can be administered by different routes. For example, administration methods that can be used for the medications according to the invention include, oral, rectal, cutaneous, pulmonary, nasal, sublingual and parenteral administration, in particular intradermic, subcutaneous, intramuscular, intravenous, intra-arterial, intrarachidian, intra-articular, intrapleural and intraperitoneal administration. In particular, when the neurological diseases are acute neurological diseases, the preferred administration routes for the medications according to the invention are intravenous, intramuscular, sublingual and cutaneous administration, preferably intravenous and intramuscular administration and, most preferably, intravenous administration. In particular, when the neurological diseases are chronic neurological diseases, the preferred administration route for the medications according to the invention is oral administration. The medications according to the invention can be administered one or more times or in continuous release, in particular in continuous perfusion.

The medications according to the invention can be in different forms, in particular in a form chosen from the group comprising tablets, capsules, pills, syrups, suspensions, solutions, powders, granules, emulsions, microspheres and injectable solutions, preferably tablets, injectable solutions, sublingual sprays and skin patches. These various forms can be obtained by methods well known to persons skilled in the art. The formulations suitable for parenteral administration, the pharmaceutically acceptable vehicles suitable for this administration route and the corresponding formulation and administration techniques can be implemented according to methods well known to persons skilled in the art, in particular those described in the manual Remington's Pharmaceutical Sciences (Mack Publishing Co., Easton, Pa., 20$^{th}$ edition, 2000).

According to another particular embodiment, 6-(benzylamino)-2(S)-[[1-(hydroxymethyl)propyl]amino]-9-isopropylpurine) or at least one of its pharmaceutically acceptable salts is present in the medication in a quantity ranging from 50 mg to 5 g per unit dose, in particular 100 mg to 2 g. The medication according to the invention can be administered in one or more doses per day, preferably in 1 to 4 doses per day. Advantageously, (S)-roscovitine can be administered in a quantity ranging from 1 to 200 mg/kg per day. Advantageously, the medication comprises a quantity of 6-(benzylamino)-2(S)-[[1-(hydroxymethyl)propyl]amino]-9-isopropylpurine) or at least one of its pharmaceutically acceptable salts ranging from 50 mg to 5 g.

According to another particular embodiment of the use according to the invention, the medication further comprises a pharmaceutically acceptable carrier. "Pharmaceutically acceptable carrier" refers to any material that is suitable for use in a pharmaceutical product. For example, pharmaceutically acceptable carriers include lactose, starch, optionally modified, cellulose, hydroxypropyl cellulose, hydroxypropylmethyl cellulose, mannitol, sorbitol, xylitol, dextrose, calcium sulphate, calcium phosphate, calcium lactate, dextrates, inositol, calcium carbonate, glycin, bentonite, polyvynylpyrrolidone and mixtures thereof. The medication according to the invention can comprise a proportion of pharmaceutically acceptable carrier ranging from 5% to 99% by weight, especially 10% to 90% by weight, and in particular 20% to 75% by weight with respect to the total weight of the composition. Other advantages and features of the invention will become apparent from the figures and examples that follow.

BRIEF DESCRIPTION OF DRAWINGS

The following figures and examples are given by way of illustration and not limitatively.

(a-c): Isolated hippocampus cells of E18 rat embryo cultivated for 10 to 15 days were characterised by immunocytochemistry with specific antibodies of different cell types and patch-clamp recording.
  (a) Photography under phase contrast microscope of cells maintained in culture for 10 days.
  (b) Fluorescence confocal microscopy photography of cells maintained under culture for 10 days and marked with anti-GFAP (red), anti-beta-tubulin of class III (green) and anti-04 (blue) antibodies. The hippocampus cultures contain both neuronal and glial cells.
  (c) Line showing voltage-clamp recordings in a full cell configuration of neurones maintained under culture for 10 days (top line) and 15 days (bottom line).

(d) A neuronal excitotoxicity model was developed using mixed hippocampus cultures of 10 days subjected to treatment by kainate. Photography under fluorescence microscope of cultures in control condition (on the left) or treated with 200 µM of kainate (on the right) and immunolabelled by the class III anti-betatubulin antibody (at the top) or by the cell death marker, propidium iodide (PI; at the bottom). Note the decrease in cell density characterised by betatubulin and the increase in cells marked by propidium iodide in the cultures treated with kainate in comparison with the control cultures.

(e) Relative percentage of cells expressing class III betatubulin in control cultures or those treated with kainate.

(f) Dose-dependent neuronal excitotoxicity of kainate. Under our conditions, treatment with 200 µM of kainate for 5 hours is necessary in order to obtain approximately 50% neuronal death (p<0.01, t-test).

DETAILED DESCRIPTION

Examples

I. Study of the Neuroprotective Effect of (S)-Roscovitine on Neuronal Death

Figure 8:
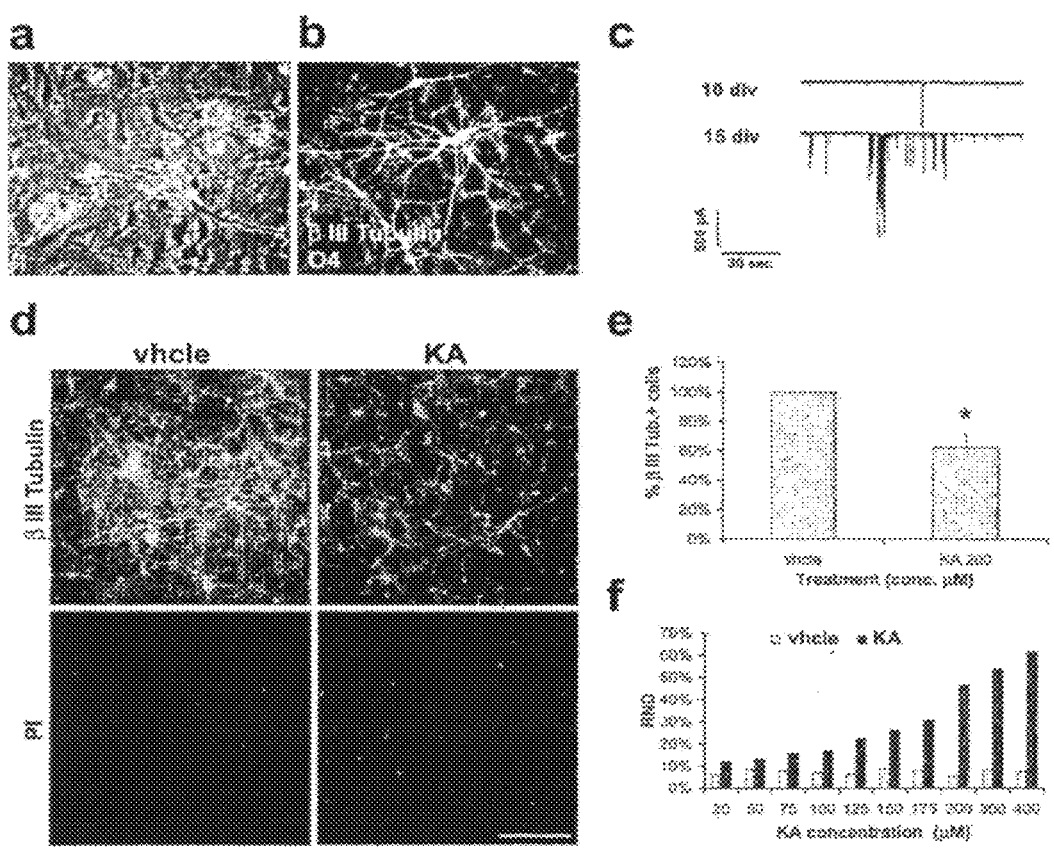
FIG. 8 illustrates the selective neuronal death caused by kainate using mixed hippocampus cultures.

I.1. Study Of The Nuroprotective Effect Of (S)-Roscovitine In An In Vitro Excitotoxicity Model: A Mixed Neural Culture Of Hippocampus Cells This model corresponds to a mixed culture of neuronal and glial cells taken from the hippocampus of rats aged 18 embryonic days (E18) and exposed to kainate (KA), a glutamate analogue. This mixed culture system was preferred to an exclusive culture system of neurones in order to better reflect the in vivo cell environment. Under these culture conditions, the astrocytes and oligodendrocytes were not affected by the kainate treatment. FIG. 8 illustrates the neurone death that was thus observed in a complex strictly neuronal excitotoxicity cell model.

Kainate, a glutamatergic agonist, was chosen in vitro as an excitotoxic agent in the present experiments. This choice was based amongst other things on in vivo studies that showed that kainate induces a programmed cell death in comparison with NMDA agonists, which induce a death of the necrotic type (Portera-Cailliau; 1997). This programmed death is also visible in acute and chronic neurological diseases. The importance and relevance of glutamate were recently emphasised by the fact that commercially available anti-glutamatergic medications are currently used in humans in Alzheimer's disease (memantine, Reisberg 3003; N. Eng. J. Med: 348: 1333-1341) and amyotrophic lateral sclerosis (Riluzol).

I.1.1. Experimental Protocol

Hippocampus cell cultures were prepared from Wistar rats aged 18 embryonic days (E18) as described in Medina et al (1994, J Neurphysiol, 72, 456-465). After 10 days of culture in vitro, the cells were incubated in the presence of kainate and/or (S)-roscovitine. The cultures were exposed for 5 hours to a 200 µM concentration of kainate. These conditions make it possible to obtain the death of 40% to 50% of the neurones in culture. (S)-Roscovitine was tested at five different concentrations (0.05 µM; 0.1 µM; 0.5 µM; 1 µM and 5 µM), alone or in combination with kainate. (S)-Roscovitine was added to the cells in culture either simultaneously with the kainate or at different times before (1 hour) or after (1, 2, or 3 hours) addition of the kainate. The cells in culture were incubated for five hours with kainate and/or the compounds to be tested before neuronal death was observed. The controls were incubated solely with the DMSO and $H_2O$ vehicles.

Neuronal death was evaluated by observation under phase contrast microscopy and by the use of propidium iodide (PI), which is a cell death marker. Propidium iodide is a red marker, which bonds specifically to the nucleic acids of the dead cells. The representative field neurons were counted. At least five fields per condition (the total number of neurones being approximately 150) were examined from 3 independent cultures. For each experimental condition, the neuronal death percentage was expressed by the ratio between the number of neurons marked by propidium iodide and the total number of neurones displaced by phase contrast microscopy.

In order to determine the neuroprotective effect of the tested compounds, the relative neuronal death (RND) was calculated and the neuroprotection index (NI) was defined as follows:

RND=% neuronal death(KA+compounds to be tested)−% neuronal death (control)/% neuronal death(KA)−% neuronal death(control) and NI=100%−RND By definition, the percentage of relative neuronal death (RND) in the cells treated with kainate alone was 100% and the neuroprotection index (NI) was 0. The concentration of tested compounds necessary for obtaining a neuroprotection index (NI) of 50% was designated CN50: neuroprotection concentration.

I.1.2 Results

I.1.2.1 Neuroprotective Effect Of (S)-Roscovitine

Figure 1:
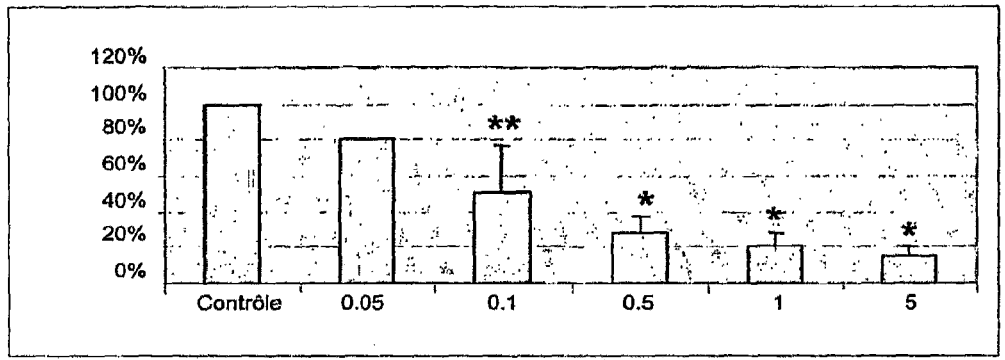
FIG. 1 is a histogram illustrating the neuroprotective effect of (S)-roscovitine in an in vitro excitotoxicity model: a mixed neural culture (astrocytes, neurones, oligondendrocytes) of hippocampus cells exposed to kainate (**$p<0.05$; *$p<0.01$ with a Student t-test).
Figure 2:
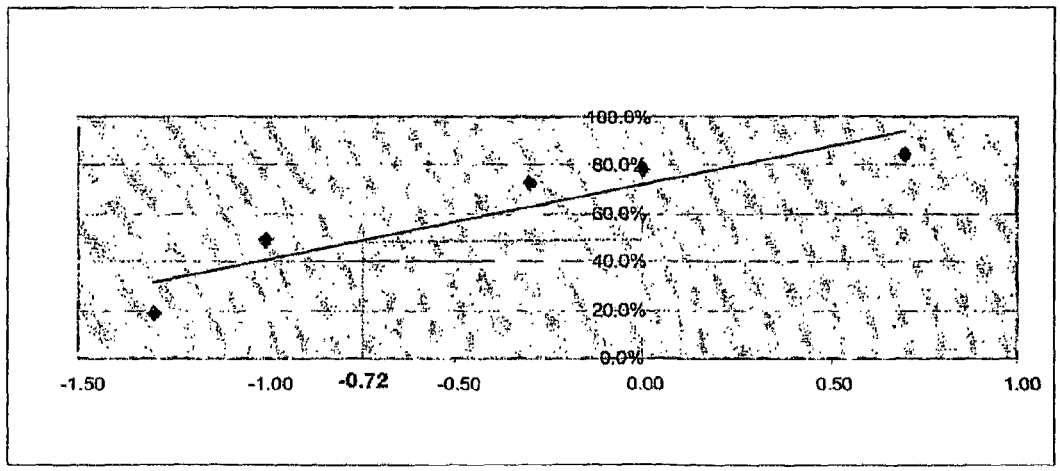
FIG. 2 is a graph illustrating the neuroprotection concentration (CN50) of (S)-roscovitine in a mixed neural culture of hippocampus cells exposed to kainate.

The effect of (S)-roscovitine on neuronal death, presented in FIG. 1, was evaluated when (S)-roscovitine is added to the middle of the culture at the same time as kainate. While the neuronal death percentage (RND) was 100% in the group treated with kainate, this was respectively 81.5%. 50.8%, 27.9%, 21.6% and 15.3% in the presence of 0.05 µM, 0.1 µM, 0.5 µM, 1 µM, and 5 µM of (S)-roscovitine. The neuroprotection index (NI) as defined previously was respectively 18.5%, 49.2%, 72.1%, 78.4% and 84.7% for doses of (S)-roscovitine of 0.05 µM, 0.1 µM, 0.5 µM, 1 µM, and 5 µM. The neuroprotective effect of (S)-roscovitine is therefore dose dependent. The neuroprotection concentration as defined previously was determined at 0.19 µM for (S)-roscovitine (FIG. 2).

Figure 3:
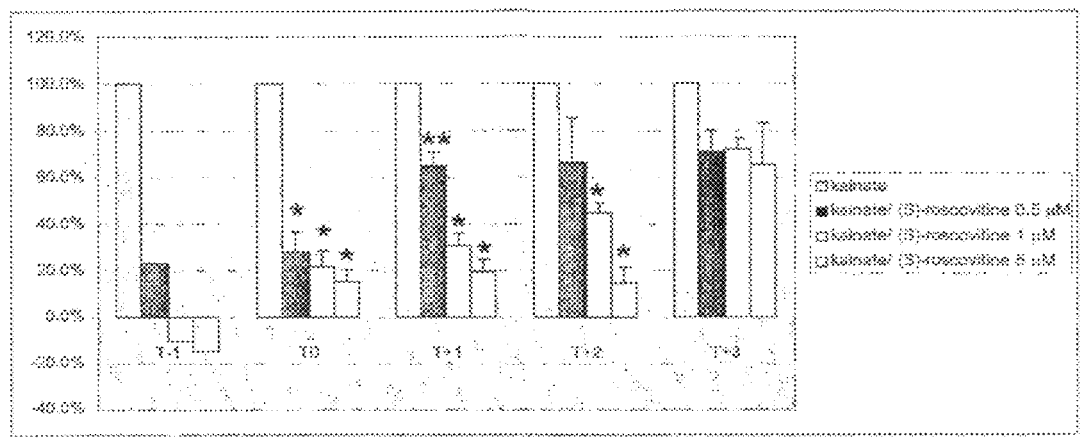
FIG. 3 is a histogram illustrating the effect of (S)-roscovitine at different incubation times on a mixed neural culture of hippocampus cells exposed to kainate (**$p<0.05$; *$p<0.01$ with a Student t-test).

I.1.2.2 Determination of the Therapeutic Window of the Neuroprotective Effect of (S)-Roscovitine The therapeutic window of the neuroprotective effect of (S)-roscovitine, presented in FIG. 3, was determined by measuring its ability to protect neurones when the compound was added to the middle of the culture either at the same time or at different times before (1 hour, T−1) or after (1 hour, 2 hours or 3 hours; T+1, T+2, T+3) the addition of kainate. Various concentrations of (S)-roscovitine were studied (0.5 µM, 1 µM and 5 µM). While the neuronal death percentage (RND) was 100% in the groups treated with kainate at the different times tested, it was respectively 23.3%, −10.4%, −14.4% at T−1, 27.9%, 21.6%, 15.3% at T0, 64.9%, 30.7%, 19.5% at T+1, 66.4%, 44.8%, 14.7% at T+2 and 71.0%, 71.7%, 65.3% at T+3 in the presence of 0.5 µM, 1 µM, and 5 µM of (S)-roscovitine. The neuroprotective index (IN) as defined previously was respectively 76.6%, 110.4%, 114.4% at T−1, 72.1%, 78.4%, 84.7% at T0, 35.1%, 69.3%, 80.5% at T+1, 33.6%, 55.2%, 85.3% at T+2, and 29.0%, 28.3%, 34.7% at T+3 for doses of (S)-roscovitine of 0.5 µM, 1 µM, and 5 µM.

The neuroprotective effect of (S)-roscovitine is observed when the compound is added to the cultures up to 2 hours after the toxic agent. In addition, the effect of (S)-roscovitine is dose dependent. Moreover, (S)-roscovitine has a preventive effect on the neuronal death caused by kainate.

I.2 Study Of The Neuroprotective Effect of (S)-Roscovitine in an In Vitro Complex Excitotoxicity Model: An Organotypical Rat Hippocampus Culture Organotypical cultures are explants of organs put in culture. These cultures have the advantage of combining control of the in vitro conditions with the complexity of the tissue, which is close to the in situ environment. Specifically, the organotypical architecture of the nerve tissue is maintained in these cultures (Stoppini et al, 1991, J Neurosci Methods, vol 37 pages 173-182). The cultures spread out considerably but remain three-dimensional, and the typical morphology of the pyramidal neurones is preserved. The synaptic organisation and the travel of the intrinsic hippocampus fibres develop in a similar manner to the in vivo situation. Likewise, the processes of maturation and formation of synapses in cultures reflect those described in vivo (Muller et al, 1993, Dev Brain Res, vol 71, pages 93-100; Buchs et al, 1993, Dev Brain Res, vol 71 pages 81-91).

I.2.1 Experimental Protocol

The organotypical cultures were carried out using hippocampus of rats aged 2 days (P2) using the method of Stoppini et al (1991, J Neurosci Methods, vol 37 pages 173-182). The rats are sacrificed by decapitation. The brain is dissected in dissection medium (PBS 1×, glucose 5.85 g/l) at 4° C. Transverse sections with a thickness of 400 µM are carried out using a tissue chopper (McIlwain). Once separated, the slices are put in culture on porous membrane (0.4 µM) and transparent membrane (30 mm diameter) inserts, in culture medium (MEM 1×, 20% horse serum, insulin 1 mg/l).

The entire culture medium is replaced every two days. The cultures are maintained at 37° C. in an incubator where the atmosphere is enriched with $CO_2$ (5%) and is humid. After 17 days in culture, the serum containing culture medium is replaced with fresh serum-free medium in the presence of propidium iodide (PI; 7.5 µM). 24 hours after the addition of PI, the medium is replaced with fresh serum-free medium containing PI and kainate (5 µM) and/or (S)-roscovitine (20 µM). The controls were incubated solely with the vehicles (DMSO and $H_2O$). The cultures are fixed after 24 hours by a 4% paraformaldehyde solution.

The cell death is quantified using propidium iodide marking with ImageJ software (NIH). The PI intensity is measured in the CA3 region for each processing condition. The neuroprotective effect is examined by determining the relative neuronal death as a parameter (RND) as defined in the previous section (I1.1).

I.2.2 Results

Figure 4:
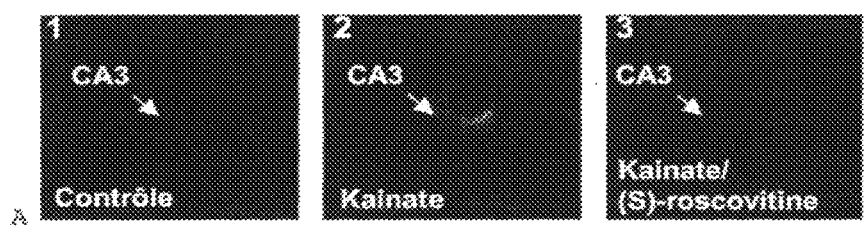
FIG. 4 (A and B) illustrates the neuroprotective effect of (S)-roscovitine in a complex in vitro excitotoxicity model: a culture of organotypical slices of rat hippocampus. (A) Observation of cell death in the CA3 rat hippocampus region after marking with propidium iodide and incubation with either DMSO and $H_2O$ (control), or kainate, or kainate and (S)-roscovitine. (B) Representation in histogram form of the relative neurone death (RND) in the CA3 rat hippocampus region after marking with propidium iodide and incubation with either DMSO and $H_2O$ (control), or kainate, or kainate and (S)-roscovitine (*$p<0.01$ with a Student t-test).
Figure 4:
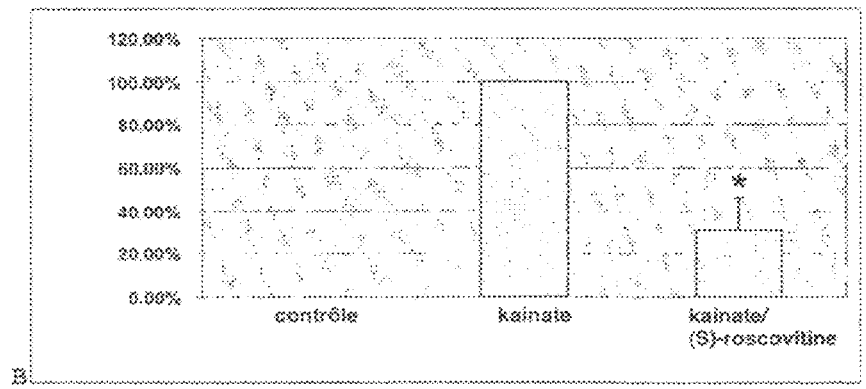

The PI fluorescence intensity is very greatly reduced in the CA3 region of the cultures treated both with kainate and (S)-roscovitine, as compared with those treated solely with kainate (FIG. 4a). Kainate-induced cell death was also quantified using ImageJ software. Our results showed that the RND is 30.7% in the presence of KA/(S)-roscovitine, whereas it is arbitrarily 100% in the presence of solely KA (FIG. 4b). These results have shown on the one hand the absence of toxic effect of (S)-roscovitine on organotypical rat hippocampus cultures, and secondly the neuroprotective effect of (S)-roscovitine on neuronal death.

I.3. Study of the Neuroprotective Effect of (S)-Roscovitine on an In Vivo Ischemia Model: A Permanent Focal Ischemia Model in Mice This model consists of the unilateral occlusion by electrocoagulation of the middle cerebral artery in adult animals (MCAo: modified method of Tamura et al, 1981, J Cereb Blood Flow, vol 1 pages 53-60). In mice, this model causes an almost exclusive attack on the temporo-parietal cortex of the ipsilateral hemisphere. These lesions are visible as soon as 3 hours after MCAo, and their size extends with time in order to reach a maximum at 24 hours (Guegan et al, 1998, Exp Neurol, vol 154 pages 371-380). At this stage, the majority of the cells located in the ischemic regions have the morphological and biochemical characteristics of apoptotic cells (Guegan et al, 1998, Exp Neurol, vol 154 pages 371-380; Guegan et al, 1998 Mol Brain Res, vol 55 pages 133-140).

I.3.1 Experimental Protocol

The ischemiae were produced on 60-days-old C57b/6 male mice weighing between 20 and 25 g according to the modified protocol of Tamura et al (1981, J Cereb Blood Flow Metab, vol 1 pages 53-60) (Guegan et al, 1998, Exp Neurol, vol 154 pages 371-380). The animals were anaesthetised with chloral hydrate (50 mg/kg). The middle cerebral artery (MCA) was surgically exposed and then electrocoagulated using a bipolar clamp. The body temperature of the animals was maintained at 30° C. throughout the surgery. The animals were sacrificed by cervical dislocation 3 hours after occlusion of the MCA.

(S)-roscovitine was administered according to two modes: intracerebroventricular and systemic. For the intracerebroventricular (ICV) route, the (S)-roscovitine was administered at a concentration of 500 µM in a solution of Kreb's Ringer using an osmotic micropump (Alzet) implanted 48 hours before the occlusion of the MCA in the right lateral ventricle of the animal at the following stereotaxic coordinates: antero-posterior=0, lateral=−0.8, depth=2 (with respect to the Bregma). Regarding the systemic route (PI), the (S)-roscovitine was administered at a concentration of 25 mg/kg in a 0.05M solution of HCl by carrying out 2 intraperitoneal injections 15 minutes before and 1 hour after the occlusion of the MCA. The control animals received only the vehicles (DMSO 1% for ICV and 0.05M HCl for the PI).

Figure 5:
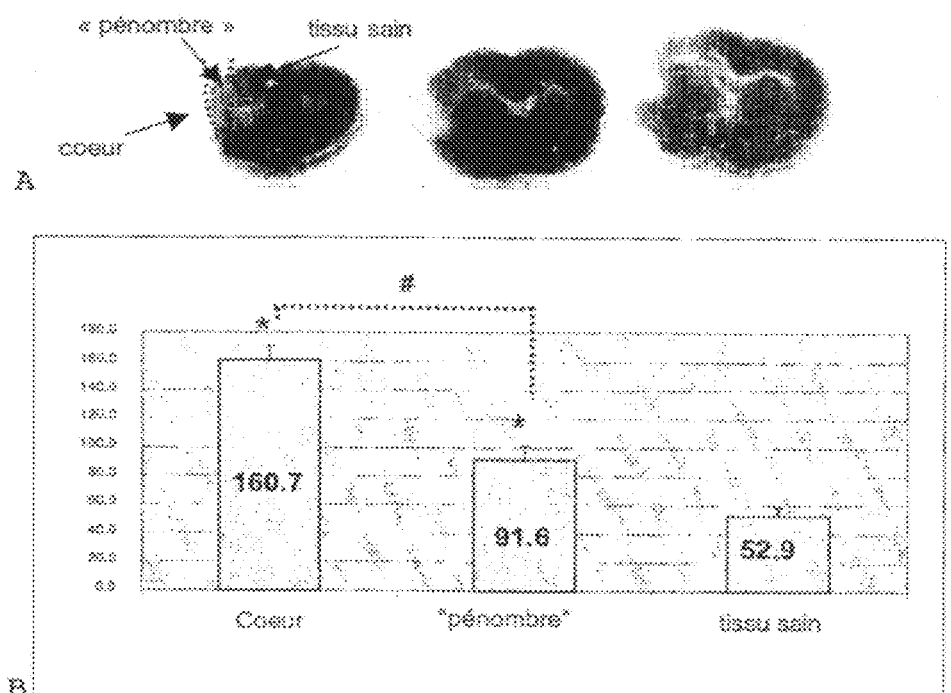
FIG. 5 (A and B) illustrates the characterisation of the "necrotic core" and "penumbra zone" regions in mouse brains in an in vivo model of permanent focal ischemia. (A) Photograph of coronal sections of an adult mouse brain coloured by 2,3,5 triphenyl tetrazolium chloride (TTC), 3 hours after MCAo. Three coronal regions can be identified and delimited according to their colouring intensity: "the necrotic core", the "penumbra zone" and healthy tissue. (B) Measurement by means of ImageJ software of the relative colouration intensities of the "necrotic core", the "penumbra zone" and the healthy tissue coloured with 2,3,5 TTC, 3 hours after MCAo. (*$p<0.01$ with a Student t-test).

The volume of the cerebral lesions was estimated using a colouring by 2,3,5 triphenyl tetrazolium chloride (TTC). This colouring is based on the correct functioning of the mitochondrial enzymes. The colouring intensity reflects the number of functional mitochondria. This colouring thus makes it possible to differentiate the injured regions from the healthy regions. The animals were sacrificed by cervical dislocation 3 hours after the occlusion of the MCA. The brains were dissected and cut into coronal slices 1 mm thick. The slices were then coloured with a solution of 1% TTC for 10 minutes and analysed using NIH ImageJ software. It was possible to determine three regions at 3 hours based on the TTC colouring intensity: a colourless necrotic core, a slightly coloured penumbra zone and a highly coloured healthy tissue (FIG. 5). The volumes of the necrotic core, the penumbra zone and the total lesion (core+penumbra) were thus determined.

I.3.2 Results

Figure 6:
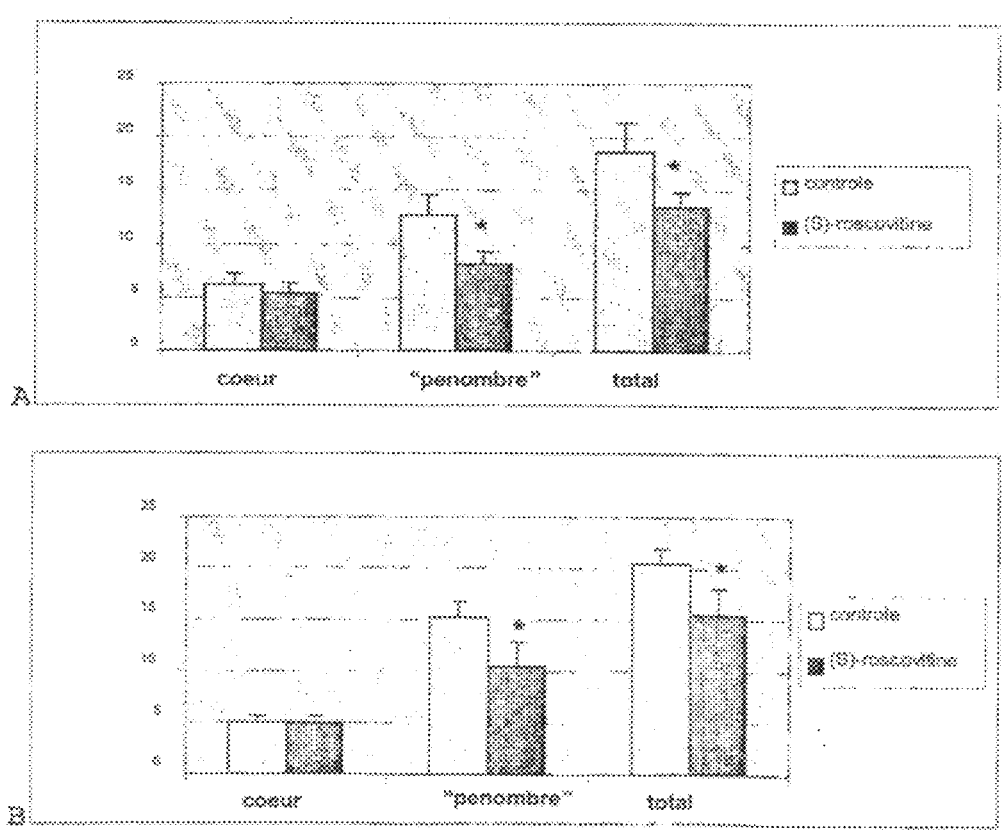
FIG. 6 (A and B) represent histograms illustrating the neuroprotective effect of (S)-roscovitine in an in vitro murine model of permanent focal ischemia. (S)-roscovitine was administered by intracerebroventricular (IVC) route (A) or systemically (PI) (B). Cell death was evaluated by measuring the relative colouring intensities in the necrotic core, the penumbra zone (*$p<0.01$ with a Student t-test).

The results are presented in FIG. 6. The administration of (S)-roscovitine by the intracerebroventricular (ICV) method caused a reduction of 27.7% in the total volume of the lesion 3 hours after the occlusion of the MCA compared with the control (18.74 mm3 for the control group and 13.54 mm3 for the group that received the (S)-roscovitine. Whereas the volume of the necrotic core remains unchanged between the two groups (6.06 mm3 for the control group and 5.39 mm3 for the group that received the (S)-roscovitine), a great reduction (35.8%) in the size of the penumbra zone was observed for the group that received the (S)-roscovitine compared with the control group (12.68 mm3 for the control group and 8.14 mm3 for the group that received the (S)-roscovitine) (FIG. 6A).

The administration of (S)-roscovitine by the systemic method (PI) caused a reduction of 30.7% in the total volume of the lesion 3 hours after the occlusion of the MCA compared with the control (20.34 mm3 for the control group and 14.10 mm3 for the group that received the (S)-roscovitine). Whereas the volume of the necrotic core remains unchanged between the two groups (5.03 mm3 for the control group and 4.88 mm3 for the group that received the (S)-roscovitine), a great reduction (38.9%) in the size of the penumbra was observed for the group that received the (S)-roscovitine compared with the control group (15.31 mm3 for the control group and 9.22 mm3 for the group that received the (S)-roscovitine) (FIG. 6B).

These results show that (S)-roscovitine has a neuroprotective effect on the volume of the lesion in a severe model of permanent focal ischemia in mice. (S)-roscovitine acts on the volume of the penumbra zone and not on the necrotic core of the lesion. In addition, these results show that (S)-roscovitine is effective after systemic administration of the compound, suggesting that (S)-roscovitine is capable of crossing the haematoencephalic barrier.

Figure 7:
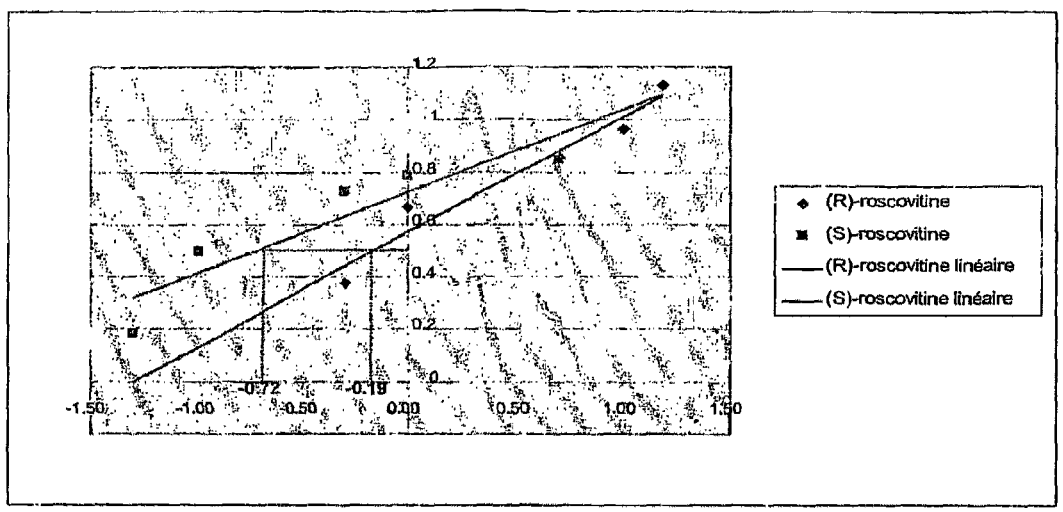
FIG. 7 illustrates the comparison of the neuroprotection index (NI) of (S)-roscovitine and (R)-roscovitine in an in vitro excitotoxicity model: a mixed neural culture of hippocampus cells exposed to kainate.

II. Comparison of the Neuroprotective Effect of (S)-Roscovitine and (R)-Roscovitine The effect of (S)-roscovitine on neuronal death has been compared with that of (R)-roscovitine in the in vitro study system as specified above at I.1. The percentage of neuronal death (RND) in the presence of (R)-roscovitine is presented in FIG. 7. (S)-roscovitine at a concentration of 0.5 µM makes it possible to obtain an RND of 27.9% whereas a concentration of 0.5 µM of (R)-roscovitine makes it possible to obtain an RND of 62%. Thus, under these conditions, (S)-roscovitine makes it possible to prevent death of twice as many neurones as (R)-roscovitine.

The concentration of neuroprotection (CN50) of (R)-roscovitine is 0.65 µM while it is 0.19 µM for (S)-roscovitine. Three times more (R)-roscovitine as (S)-roscovitine is therefore necessary to prevent the death of the same number of neurones. These experiments show clearly that the neuroprotective effect of (S)-roscovitine is greater than that of (R)-roscovitine.

The invention claimed is:

1. A method for protecting against and/or treating neurological diseases associated with excitotoxic neurological lesions, comprising administering to a subject in need thereof a pharmaceutically effective amount of a composition comprising roscovitine in an enantiomeric excess of greater than or equal to 90% of 6-(benzyl-amino)-2(S)-[[1-(hydroxymethyl)propyl]amino]-9-isopropylpurine) or at least one of its pharmaceutical acceptable salts.

2. The method of claim 1, wherein the neurological diseases are chronic or acute neurological diseases.

3. The method of claim 2, wherein the acute neurological disease is epilepsy; status epilepticus; stroke; cerebral haemorrhages; cerebral hypoxia during cardiac arrests; cranial traumatisms; or neurological diseases causing focal and/or global cerebral hypoxia.

4. The method of claim 3, wherein the cerebral haemorrhages are associated with the use of a thrombolytic agent.

5. The method of claim 4, wherein the thrombolytic agent is a tissue plasminogen activator.

6. The method of claim 1, wherein the neurological diseases are neurodegenerative diseases.

7. The method of claim 6, wherein the neurodegenerative diseases comprise diseases with an extrapyramidal syndrome and dementias.

8. The method of claim 6, wherein the neurodegenerative diseases comprise Parkinson's disease, progressive supranuclear paralysis (Steel-Richardson and Olzewski syndromes), multiple system atrophy, striatonigral degeneration, Alzheimer's disease, vascular dementias, Lewy body disease, fronto-temporal dementias, cortico-basal degeneration, Huntington's chorea, amyotrophic lateral sclerosis and Creutzfeld-Jakob disease.

9. The method of claim 1, wherein the roscovitine or at least one of its pharmaceutical acceptable salts is administered in combination with at least one anti-neurodegenerative agent.

10. The method of claim 9, wherein the anti-neurodegenerative agent is donepezil, selegiline, rivastigmine, galantamine, memantine or riluzole.

11. The method of claim 1, wherein the roscovitine or at least one of its pharmaceutical acceptable salts is administered in combination with at least one thrombolytic agent.

12. The method of claim 11, wherein the thrombolytic agent is a tissue plasminogen activator, a streptokinase, urokinase or desmoteplase.

13. The method of claim 1, wherein or at least one of its pharmaceutical acceptable salts is administered in combination with at least one platelet aggregation inhibiting agent.

14. The method of claim 13, wherein the platelet aggregation inhibiting agent is aspirin, ticlopidine, clopidogrel, persantine, abciximab or flurbiprofen.

15. The method of claim 1, wherein the roscovitine or at least one of its pharmaceutical acceptable salts is administered by oral, rectal, cutaneous, pulmonary, nasal, sublingual or parenteral administration.

16. The method of claim 15, wherein the administration is intradermic, subcutaneous, intramuscular, intravenous, intraarterial, intrarachidian, intra-articular, intrapleural or intraperitoneal administration.

17. The method of claim 1, wherein the roscovitine or at least one of its pharmaceutical acceptable salts is administered in the form of a tablet, capsule, pill, syrup, suspension, solution, powder, granule, emulsion, microsphere, injectable solution, sublingual spray or skin patch.

18. The method of claim 1, wherein the pharmaceutical composition comprises from 100 mg to 5 g of the roscovitine or at least one of its pharmaceutical acceptable salts per unit dose.

19. The method of claim 18, wherein the pharmaceutical composition comprises from 100 mg to 2 g of the roscovitine or at least one of its pharmaceutical acceptable salts per unit dose.

20. The method of claim 1, wherein the pharmaceutical composition further comprises a pharmaceutically acceptable carrier.

* * * * *